(12) United States Patent
Al-Ali

(10) Patent No.: US 8,255,026 B1
(45) Date of Patent: Aug. 28, 2012

(54) PATIENT MONITOR CAPABLE OF MONITORING THE QUALITY OF ATTACHED PROBES AND ACCESSORIES

(75) Inventor: Ammar Al-Ali, Tustin, CA (US)

(73) Assignee: Masimo Corporation, Inc., Irvine, CA (US)

( * ) Notice: Subject to any disclaimer, the term of this patent is extended or adjusted under 35 U.S.C. 154(b) by 1295 days.

(21) Appl. No.: 11/871,817

(22) Filed: Oct. 12, 2007

Related U.S. Application Data

(60) Provisional application No. 60/851,788, filed on Oct. 12, 2006.

(51) Int. Cl.
A61B 5/1455 (2006.01)

(52) U.S. Cl. .................. 600/310; 600/322; 600/323

(58) Field of Classification Search .......... 600/310, 600/322–324, 331, 436–437, 473, 476
See application file for complete search history.

(56) References Cited

U.S. PATENT DOCUMENTS

| | | | |
|---|---|---|---|
| 4,942,877 A * | 7/1990 | Sakai et al. ............... | 600/323 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| 5,720,293 A * | 2/1998 | Quinn et al. ............... | 600/505 |
| D393,830 S | 4/1998 | Tobler et al. | |
| 5,743,262 A | 4/1998 | Lepper, Jr. et al. | |
| 5,758,644 A | 6/1998 | Diab et al. | |

(Continued)

*Primary Examiner* — Eric Winakur
*Assistant Examiner* — Chu Chuan (JJ) Liu
(74) *Attorney, Agent, or Firm* — Knobbe Martens Olson & Bear LLP

(57) ABSTRACT

A system and method to help maintain quality control and reduce cannibalization of accessories and attached probes in a highly sensitive patient monitor, such as a pulse oximetry system. One or more attached components may have information elements designed to designate what quality control mechanisms a patient monitor should look to find on that or another component or designate other components with which the one component may properly work. In a further embodiment, such information elements may also include data indicating the appropriate life of the component.

19 Claims, 7 Drawing Sheets

U.S. PATENT DOCUMENTS

| | | | |
|---|---|---|---|
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,014,576 A * | 1/2000 | Raley .................... 600/322 |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,351,658 B1 * | 2/2002 | Middleman et al. .......... 600/331 |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| 7,280,858 B2 | 10/2007 | Al-Ali et al. |

* cited by examiner

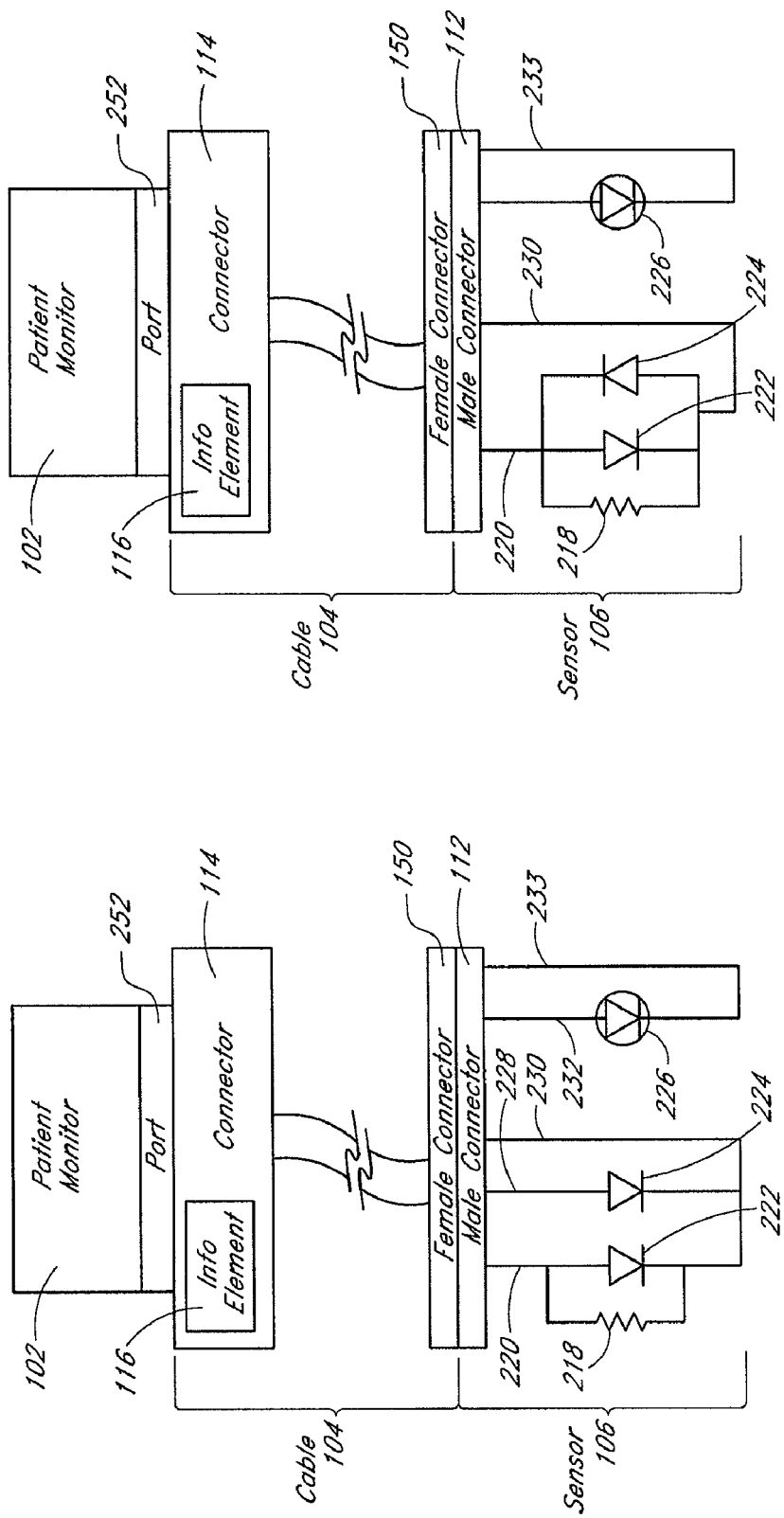

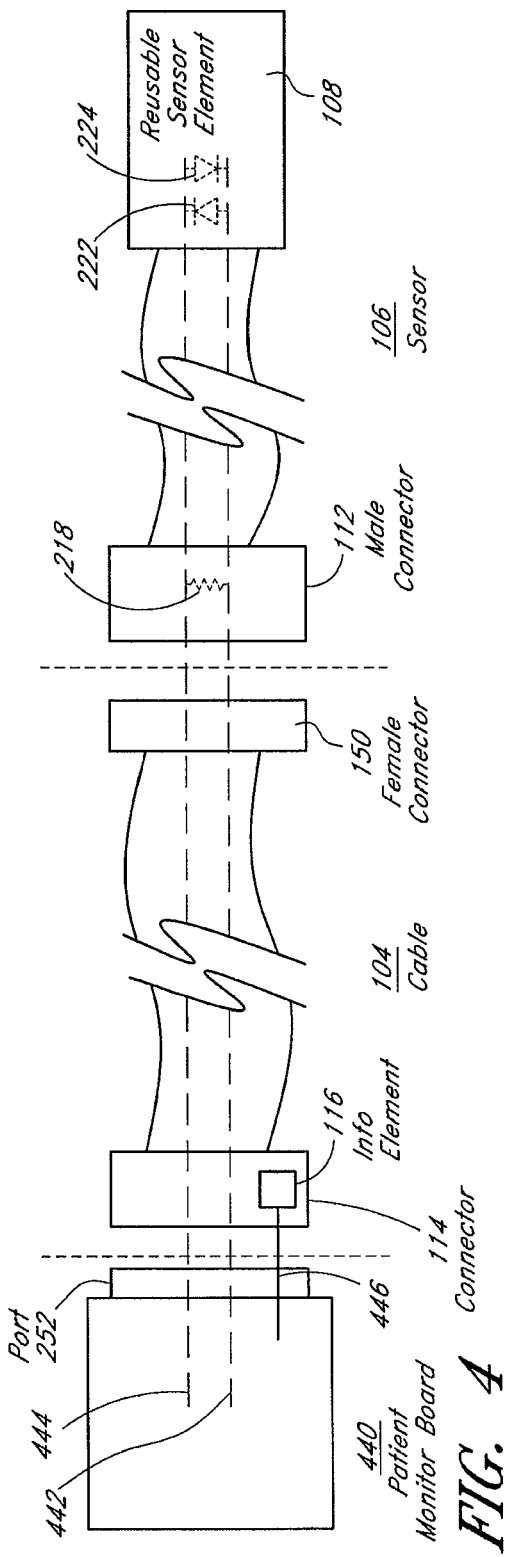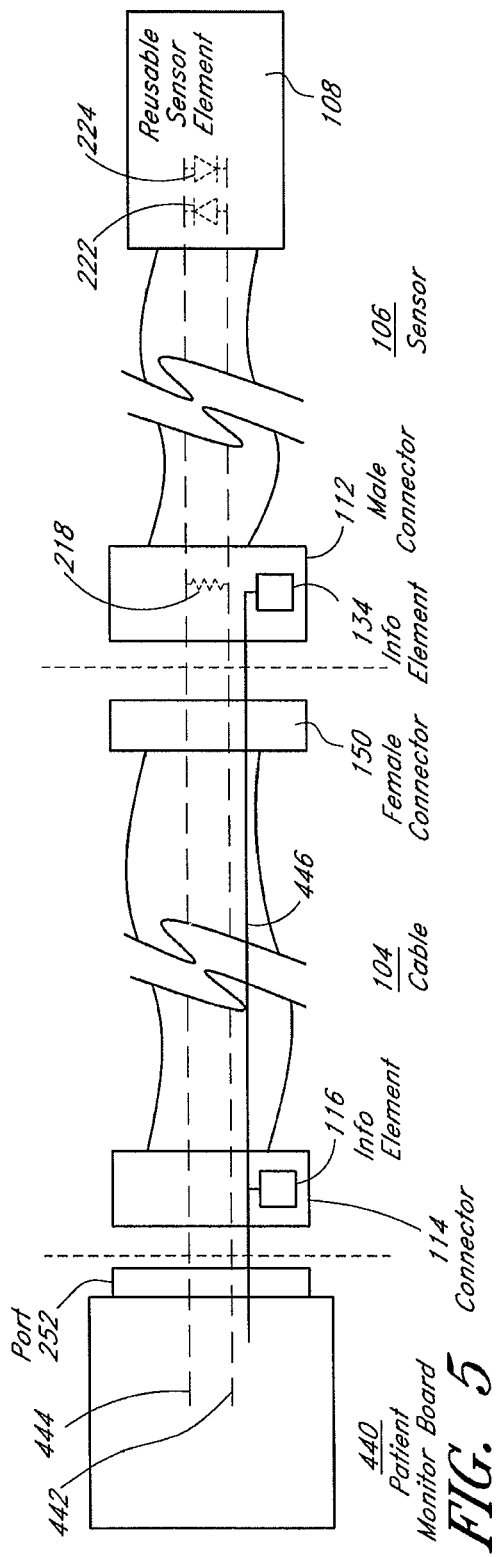

PATIENT MONITOR CAPABLE OF MONITORING THE QUALITY OF ATTACHED PROBES AND ACCESSORIES

PRIORITY CLAIM

This application claims priority to U.S. Provisional Application No. 60/851,788, titled "Patient Monitor Capable of Monitoring the Quality of Attached Probes and Accessories" and filed on Oct. 12, 2006, the disclosure of which is incorporated herein by reference.

CROSS-REFERENCE TO RELATED APPLICATIONS

This application is related to U.S. patent application Ser. No. 11/640,077, filed on Dec. 12, 2006, which is a continuation of U.S. patent application Ser. No. 10/757,279, filed on Jan. 13, 2004, which is a continuation of Ser. No. 10/005,711, filed on Nov. 8, 2001, now U.S. Pat. No. 6,678,543, which is a continuation of U.S. patent application Ser. No. 09/451,151, filed on Nov. 30, 1999, now U.S. Pat. No. 6,397,091, which is a continuation of U.S. patent application Ser. No. 09/016,924, filed on Feb. 2, 1998, now U.S. Pat. No. 6,011,986, which is a continuation of U.S. patent application Ser. No. 08/478,493, filed on Jun. 7, 1995, now U.S. Pat. No. 5,758,644, as well as U.S. patent application Ser. No. 08/745,474, filed on Nov. 12, 1996, now U.S. Pat. No. 5,823,950, which is a divisional of U.S. U.S. patent application Ser. No. 08/478,493, filed on Jun. 7, 1995, now U.S. Pat. No. 5,758,644. The present application incorporates the foregoing disclosures herein by reference.

BACKGROUND OF THE DISCLOSURE

1. Field of the Disclosure

The present disclosure relates in general to noninvasive patient monitoring systems, including oximeters and co-oximeters, and their accessories such as sensors or cables. In particular, this disclosure relates to patient monitors capable of monitoring the quality of attached accessories.

2. Description of the Related Art

Patient monitoring of various physiological parameters of a patient is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a sensor attached externally to a patient to output signals indicative of various physiological parameters, such as a patient's constituents or analytes, including for example a percent value for arterial oxygen saturation, carbon monoxide saturation, methenoglobin saturation, fractional saturations, total hematocrit, billirubins, perfusion quality, or the like A pulse oximeter sensor generally includes one or more energy emission devices, such as specific wavelength emitting LEDs, and one or more energy detection devices. The sensor is generally attached to a measurement site such as a patient's finger, toe, ear, ankle, or the like. An attachment mechanism positions the emitters and detector proximal to the measurement site such that the emitters project energy into the tissue, blood vessels and capillaries of the measurement site, which in turn attenuate the energy. The detector then detects that attenuated energy. The detector communicates at least one signal indicative of the detected attenuated energy to a signal processing device such as an oximeter, generally through cabling attaching the sensor to the oximeter. The oximeter generally calculates, among other things, one or more physiological parameters of the measurement site. In some oximeter systems, specific-valued resistors in the attached sensor provide the signal processing device specific wavelength ("$\lambda$") information for the emitters of the sensor. For example, oximeters that capture $\lambda$ information are disclosed in U.S. Pat. No. 4,621,643, entitled "Calibrated Optical Oximeter Probe" and awarded to New, Jr. et al. on Nov. 11, 1986, and U.S. Pat. No. 4,700,708, entitled "Calibrated Optical Oximeter Probe" and awarded to New, Jr. et al. on Oct. 20, 1987.

Patient monitors, generally, and oximeter systems specifically are often highly sensitive instruments. This is especially the case in oximeter systems capable of determining physiological parameters during patient motion, such as those commercially available from Masimo Corporation of Irvine, Calif., and disclosed generally in U.S. Pat. Nos. 6,263,222, entitled "Signal Processing Apparatus," and 6,157,850, also entitled "Signal Processing Apparatus," U.S. application Ser. No. 09/491,175, entitled "Universal/Upgrading Pulse Oximeter," and the like, each of which is incorporated herein by reference. The manufacturers of such oximeter systems incorporate into their signal processing algorithms an expectation of a certain type and quality of electronic components in the cabling and sensors. Often the results produced by the signal processing, such as, for example, the output values of various monitored physiological parameters of the patient, are at least somewhat dependent upon receipt of signals from quality electronic components. Thus, many manufacturers carefully control and manage the type and quality of their sensors and accessories.

However, when other sensor manufacturers lure caregivers into purchasing "compatible" sensors, the oximeter manufacturer loses the ability to control the type and quality of the electronic components, the accuracy of their attachment/placement mechanisms, and the like. This is especially problematic with knock-off accessories that attempt to standardize sensor components across differing manufacturers' oximeter systems. For this reason, oximeter manufactures began using the foregoing resistors also as quality control security devices. For example, some oximeter systems look for specific-valued resistors within the circuitry of their sensors, such as, for example, those resistors disclosed in patents entitled "Manual and Automatic Probe Calibration:" U.S. Pat. No. 5,758,644, awarded to Diab et al. on Jun. 2, 1998; U.S. Pat. No. 6,011,986, awarded to Diab et al. on Jan. 4, 2000; and U.S. Pat. No. 6,397,091, awarded to Diab et al. on May 28, 2002. Although such resistor mechanisms improved manufacturer's quality control, some knock off sensor manufactures unfortunately began copying or otherwise scavenging quality control devices from, for example, expired or authorized sensors, thus defeating the quality control device of the original oximeter manufacturer.

Additionally upgrades to patient monitor algorithms and specifications may be made with the expectation that accessories with different optics, higher fidelity, different specifications or the like will be used. A quality check in such an instance can help to ensure that any upgraded algorithms produce more accurate results.

SUMMARY OF THE DISCLOSURE

Based on at least the foregoing, there is a need to provide oximetry systems capable of monitoring the quality of attached optical probes and accessories, while reducing the ability of unscrupulous sensor manufacturers to defeat such quality controls. Accordingly, one aspect of the present disclosure is a patient monitoring system for maintaining quality control while reducing a likelihood of defeat of that quality control, through, for example, cannibalization of quality control devices from used and possibly damaged authorized sensors. According to an embodiment of the disclosure, an oximetry system includes an oximeter, a sensor, and a connecting cable to connect the sensor to the oximeter. In an embodiment, the cable includes an information element capable of storing information. The cable's information element could be provided through an active circuit such as a transistor network, memory chip, EEPROM (electronically erasable programmable read-only memory), EPROM (erasable programmable read-only memory), or other identification device, such as multi-contact single wire memory devices or other devices, such as those commercially available from Dallas Semiconductor or the like. In an embodiment, the oximeter accesses the information stored on the information element of the cable to determine whether the cable is an authorized cable.

In an embodiment, the oximeter may use the information stored on the cable information element to determine a type of quality control device expected on an attached sensor. For example, one type of information may advantageously instruct the oximeter to look for a quality control device comprising a sensor identifier, for example, a resistor of a specified value on the sensor. Another type of information may advantageously instruct the oximeter to look for a different quality control device comprising, for example, a sensor information element storing additional identifying information. In the event that the oximeter fails to find one or more of the information element on the cable and the quality control device(s) on the sensor, the oximeter may take one or more remedial actions, such as, for example, activating audio or visual alarms, combinations of the same, or the like. In an embodiment, the oximeter may display an alarm message such as "unrecognized sensor," "unauthorized sensor" "unrecognized cable," "unauthorized cable," or the like.

Another aspect of the present disclosure is a method for testing a sensor. The method comprises obtaining first information from a first information element, outputting a signal to the sensor based on the first information, receiving one or more responses from the sensor, and determining whether the one or more responses from the sensor indicate the sensor comprises an authorized sensor.

In yet other embodiments, encryption algorithms may advantageously encrypt information stored on one or more of the various information elements and/or encrypt the communication to and from the oximeter. A skilled artisan will recognize from the disclosure herein that a wide variety of simple or complex encryption algorithms, paradigms, methodologies, or a combination of the same could be used to further inhibit copyist sensor manufacturers attempting to produce "compatible" sensors outside the quality control of the oximeter provider. Examples can include the use of translation tables, symmetric or asymmetric key-based encryption methods, or many other encryption techniques or combinations known to an artisan of ordinary skill.

In yet a further embodiment, the oximeter may further store information regarding the useful and safe life of electrical components of, for example, the sensor, the cabling, or the like. For example, the amount of use of a particular component may advantageously be tracked to reduce overuse of that component. Monitoring of overuse is especially advantageous in reusable technologies, and may be accomplished, for example, as disclosed in U.S. Pat. No. 6,515,273 entitled "System for Indicating the Expiration of the Useful Operating Life of a Pulse Oximetry Sensor," awarded to Al-Ali, owned by the assignee of the present disclosure and incorporated herein by reference. In such systems, the oximeter systems may advantageously be capable of identifying source-indicating elements in an attached cabling and/or sensor, and how long various sensor elements have been in use. Thus, should an unauthorized sensor manufacturer manage to scavenge some or all of the identifying parts of a used sensor according to this embodiment, the useful life measurement may advantageously significantly reduce any extended use of any cannibalized sensor. For example, in some embodiments, the useful life of electronic components of a sensor may be measured in weeks of use, thereby significantly limiting the value of scavenged components to knock-off sensor manufacturers. Reduction of scavenged value advantageously increases the ability of sensor manufacturers to control the quality of sensor components and oximeter accessories.

In addition, in another embodiment, attached accessories, such as cabling and/or sensors, may have an information element that can store data from an oximeter or other patient monitor. In such an embodiment, each oximeter or patient monitor has a software ID. When an accessory is attached, the monitor looks to see if any monitor has written to the accessory's information element. If not, in an embodiment, the monitor stores its software ID on the accessory. In a possible embodiment, use of an accessory which has had a monitor ID written to it may only be enabled if the accessory is attached to the monitor having the same ID or some defined set of monitors having software IDs in a specific set that includes the monitor ID written to it.

Yet another embodiment may utilize similar principles in controlling the upgrading of patient monitors. In an embodiment, a patient monitor is capable of monitoring a wide array of patient parameters, but the monitoring of individual parameters may be enabled or disabled based on the parameter monitoring licensed to the user. It will be advantageous to allow changes to the enabled parameters without returning the patient monitor to the manufacturer. In an embodiment, this may be done by connecting an upgrade tool much like any other accessory discussed herein. In an embodiment, the ability to upgrade a given patient monitor is dependent on an ID on the upgrade tool matching or corresponding to an allowed monitor ID.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

The following drawings and the associated descriptions are provided to illustrate embodiments of the present disclosure and do not limit the scope of the claims.

FIG. 2 illustrates an exemplary block diagram of an oximetry system including quality control devices, according to an embodiment of the disclosure.

FIG. 2A illustrates another exemplary block diagram of an oximetry system including quality control devices, according to an embodiment of the disclosure.

FIG. 4 illustrates an exemplary block diagram of an oximetry system including quality control devices, according to an embodiment of the disclosure.

FIG. 5 illustrates an exemplary block diagram of an oximetry system including quality control devices, according to an embodiment of the disclosure.

DETAILED DESCRIPTION

Figure 1:
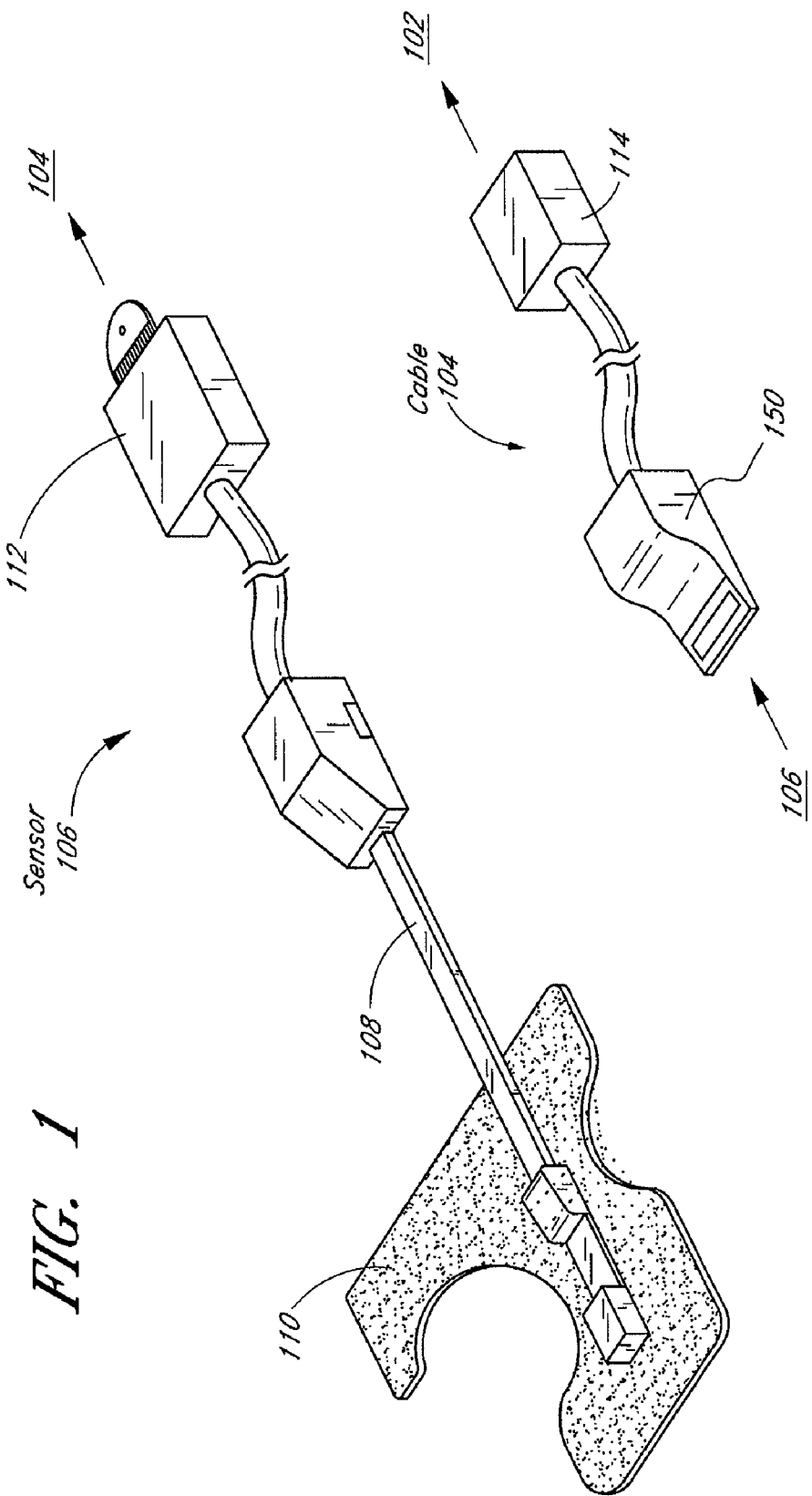
FIG. 1 illustrates a perspective view of a typical sensor including reusable and disposable elements, and a typical cable.

The present disclosure has applicability to medical probes in general and is directed toward patient monitors, cabling, sensors, and the like. As discussed above, a patient monitor comprises signal processing capable of monitoring whether a caregiver or user is attaching authorized cabling and/or sensors. Such quality control systems aid monitor manufacturers in ensuring that caregivers such as doctors obtain accurate data from patient monitors used in applications from general ward, athletic, or personal monitoring to surgical and other potentially life-threatening environments, to any other use of noninvasive monitoring of patient physiologies. Although the present disclosure is applicable to many different types of patient monitors, some of this discussion will focus on pulse oximeters, as representative embodiments only.

In general, a patient monitor may advantageously read a first information element on a first accessory to obtain first quality control information. The first information may advantageously allow the signal processor to identify the first accessory, such as a cable, as an authorized cable. In an embodiment, the patient monitor may advantageously read a second information element on a second accessory to obtain second quality control information. In an embodiment, the first information element provides an indication of what the second quality control information should be. When the first and second information correlates, the patient monitor can be more assured of the quality of the attached accessories. On the other hand, when there is a mismatch, various remedial measures may be taken, including displaying a message of one or more unauthorized accessories, actuating an indicator light on one or more of the accessories, or other audible or visual indications of the mismatch.

For example, in an embodiment, a signal processor of a patient monitor communicates with a first information element associated with a first accessory, and uses the information stored or coded therein to determine a type of information such as a resistance value, expected to be stored or coded into a second information element associated with a second accessory. Specifically, the information gained from the first accessory, such as a cable, may provide specific resistance value(s) or range of values expected on the second accessory, such as a sensor. Such resistance values may be found in parallel with one or more emitters (such as for example, those disclosed in the foregoing '644 patent) or on separate conductors (such as, for example, those disclosed in the foregoing '643 patent). In other embodiments, the information gained from the first accessory provides information usable to access the second information element. Communication with the second information element on the second accessory advantageously provides the specific resistance value(s) or range of values expected on the sensor.

In another embodiment, the patient monitor may advantageously additionally acquire information indicative of the lifespan, amount of use, or age of one or more accessories, including the cable and/or the sensor. In an embodiment, if the patient monitor determines that one or more accessories have expired, it will inform the user with an appropriate audio or visual message.

Much of this discussion utilizes pulse oximeters and oximeter cable and sensor accessories in explaining the disclosure and for ease of understanding. However, the disclosure herein is not limited thereby. Patient monitors other than oximeters may similarly utilize the ideas disclosed. Similarly, labeling the first and second accessories as a cable and sensor more clearly differentiate the two accessories; however, a skilled artisan will recognize, from the disclosure herein, a wide range of uses of cascading security devices for linked or nonlinked monitor accessories.

To facilitate a complete understanding of the disclosure, the remainder of the detailed description describes the disclosure with reference to the drawings. Corresponding numbers indicate corresponding parts, and the leading digit of any number indicates the figure in which that element is first shown.

FIG. 1 shows sensor and cable elements of an oximeter system as is generally known in the prior art. The system comprises cable 104 connecting sensor 106 to an oximeter 102 (not shown). As shown here, the sensor 106 includes a reusable portion 108, generally including expensive electronics, and a disposable portion 110, generally including positioning mechanisms such as tape. Male connection housing 112 at one end of sensor 106 connects sensor 106 to female cable connection 150 of cable 104. The operation and construction of reusable and disposable sensors is disclosed in U.S. Pat. No. 6,920,345 entitled "Optical Sensor Including Disposable and Reusable Elements" awarded to Al-Ali and owned by the assignee of the present disclosure, the full disclosure of which is incorporated herein by reference. Other disclosure may be found in U.S. Application No. 60/740,541, filed Nov. 29, 2005, also entitled "Optical Sensor Including Disposable and Reusable Elements," incorporated herein by reference.

Figure 1B:
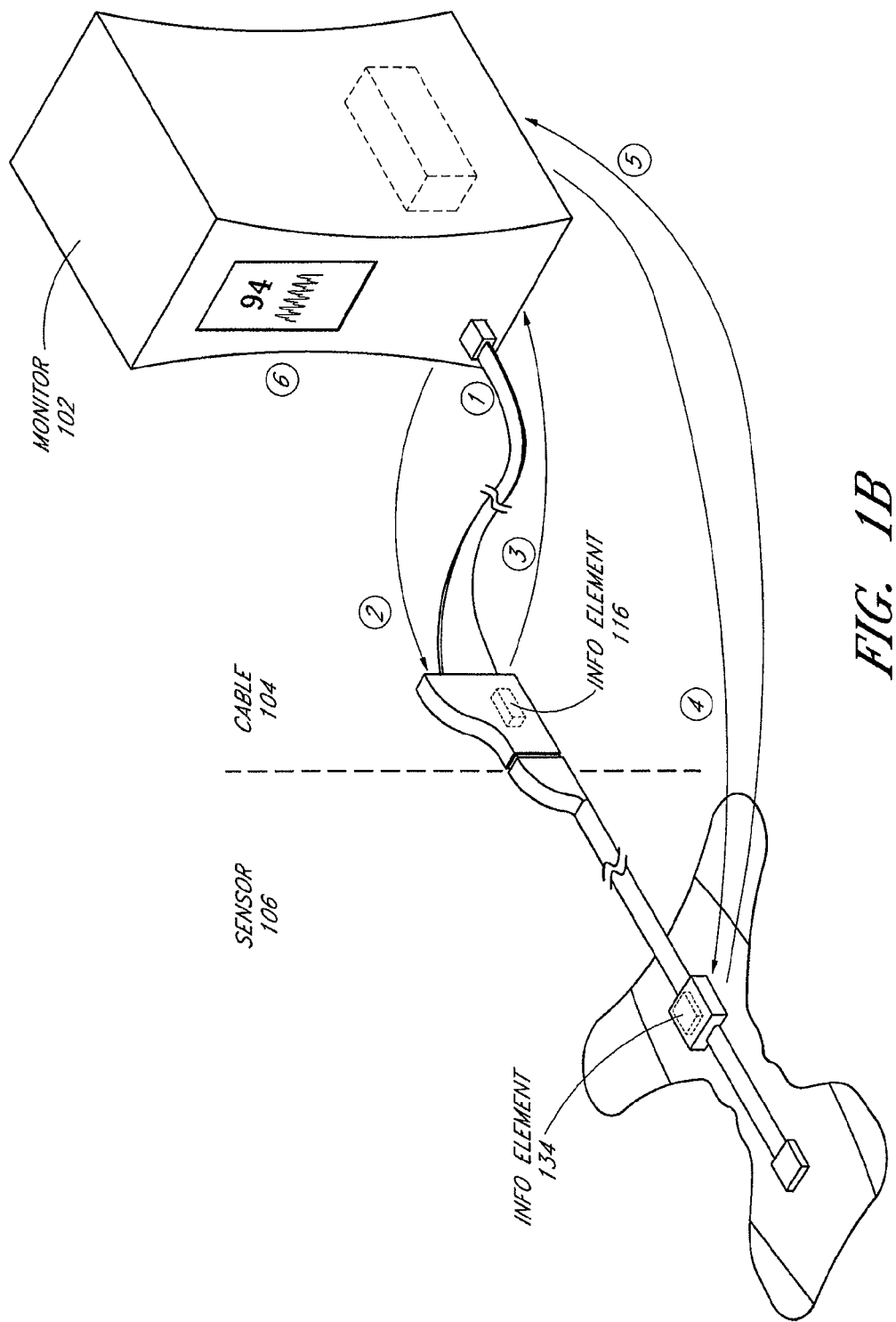
FIG. 1B illustrates the signal flow of an embodiment of a method of utilizing quality control elements to monitor authorized accessories according to this disclosure.

FIG. 1B illustrates a patient monitor 102 and attached accessories in accordance with an embodiment of the disclosure. Specifically, cable 104 and sensor 106 each include an information element housed within them (cable information element 116 and second sensor information element 134, respectively). The placement of these information elements need not be as shown in the figure, as will be described in more detail below. FIG. 1B also illustrates the signal flow of an embodiment of a process for controlling the quality of attached accessories. First, the quality control process may be initiated when one or more new accessories are attached to the monitor 102; similarly, the process may initiate when a monitor is turned on. Recognizing that an accessory is attached, the monitor searches for cable information element 116 (step 2). The information element 116 then returns a cable authentication code, which may be used by the monitor to determine that the cable 104 is a quality, authorized cable (step 3). Based on the cable authentication code, the monitor 102 then searches for a specific sensor information element 134 (step 4). If the correct type of information element is found, the monitor retrieves a sensor authorization code (step 5). The monitor can then compare the cable authorization code and the sensor authorization code to determine whether the cable 104 and sensor 106 are matching, quality accessories. If the codes do correlate, the monitor may enable the system for monitoring of a patient (step 6).

FIGS. 2 and 2A show a block diagram of embodiments of oximeter systems including improved security technologies. Oximeter 102 uses port 252 to connect to cable 104 at connector 114. Cable 104 in turn uses cable connector 150 to connect to sensor 106 at connection housing 112. Cable 104 includes an information element 116, which may be located anywhere therein, but is pictured in the figures in port connector 114. Cable information element 116 is preferably an EEPROM with encrypted data. In an embodiment, sensor 106 includes LEDs 222 and 224. The first LED 222 has a first corresponding electrical connection 220; the second LED 224 has a second corresponding electrical connection 228; and the photodetector 226 has a corresponding electrical connection 232. In the configuration shown in FIG. 2, the LEDs 222, 224 are connected at their outputs to a common ground electrical connection 230; however, other configurations may advantageously be implemented, such as, for example back-to-back (see FIG. 2A), anode, cathode, common anode, common cathode, or the like. The photodetector 226 is connected to an electrical connection 233. In accordance with this aspect of the present disclosure, one of the LED electrical connections 220 can also be used for a first sensor information element 218—placing first sensor information element 218 in parallel with one of LEDs 222, 224. In an embodiment, first sensor information element may comprise a coding resistor or other passive element.

According to an embodiment, Oximeter 102 may communicate with cable information element 116 which returns data to oximeter 102. In at least an embodiment such data may be encrypted, and oximeter 102 is able to decrypt the information. In an embodiment, the information designates additional information that oximeter 102 may read from attached sensor 106, generally from first sensor information element 218. The value of the first sensor information element 218 and/or its placement across an LED may be used to help indicate that the probe is configured properly for the oximeter. The first sensor information element 218 may be utilized to indicate that the probe is from an authorized supplier such as a "Masimo" standard probe, "Patient Monitoring Company 1" probe, "Patient Monitoring Company 2" probe, etc. In another embodiment, the first sensor information element 218 may be used to indicate LED wavelengths for the sensor or other parameters of the sensor 106.

In an embodiment, reading of the first sensor information element 218 may advantageously be accomplished according to the disclosure of U.S. Pat. No. 6,397,091, entitled "Manual and automatic probe calibration," awarded to Diab and owned by the assignees of the present disclosure, incorporated herein by reference.

In addition, it should be noted that the cable information element or first sensor information element need not be passive elements. Coding information could also be provided through an active circuit such as a transistor network, memory chip, or other identification device, for instance Dallas Semiconductor DS 1990 or DS 2401 or other automatic identification chip. It is also possible to place the first sensor information element 218 in series or in parallel with one of the LEDs 222, 224 or with the photodetector 226 on transmission line 233 or place the first sensor information element 218 apart from all of the LEDs 222, 224 and photodetector 226 on its own transmission lines. Other placements of the first sensor information element 218 would also be obvious to one of ordinary skill in the art, so long as the coded value or other data from first sensor information element 218 can be determined by oximeter 102.

Figure 3:
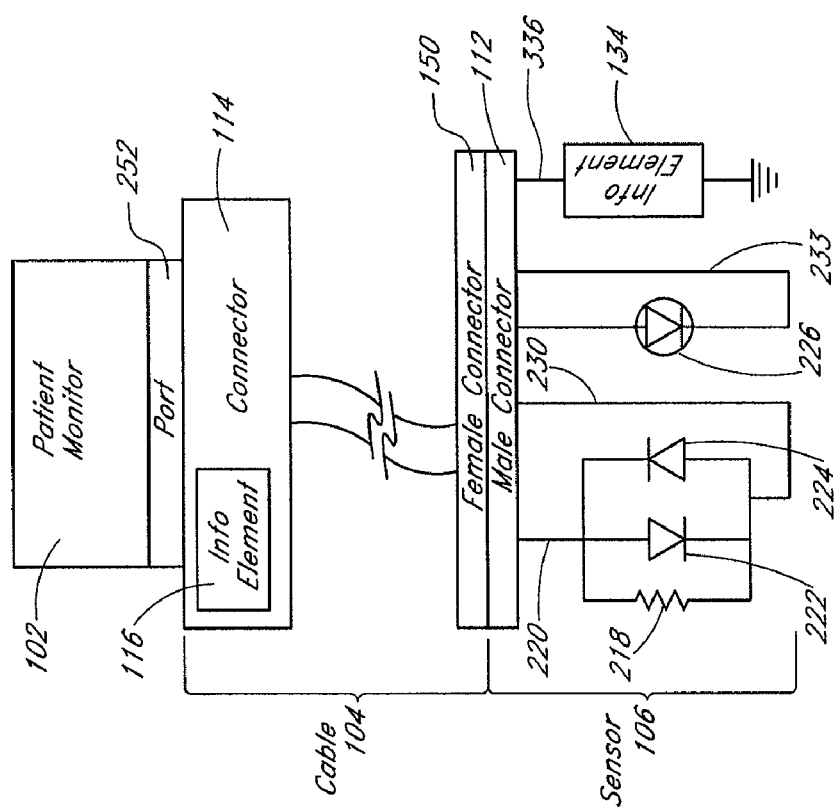
FIG. 3 illustrates another exemplary block diagram of an oximetry system including quality control devices, according to an embodiment of the disclosure.

Another embodiment of an oximeter system having improved security technologies is shown in FIG. 3. In embodiments such as pictured in FIG. 3, sensor 106 of the oximeter system additionally has a second sensor information element 134. In a preferred embodiment, second sensor information element 134 is an EEPROM with encrypted data, but it may be any of a wide variety of active or passive solutions discussed in relation to first sensor information element and/or cable information element. The second sensor information element 134 is attached to the sensor through line 336. Line 336 may preferably be a serial cable or other type of cable that allows two-way transfer of data. In such an embodiment, cable information element 116 of the cable may provide information to oximeter 102 that indicates both a first sensor information element 218 and a second sensor information element 134 should be found and provide information to the oximeter 102. Second sensor information element 134 may then provide data, encrypted or not, to oximeter 102, such that the data indicates to oximeter 102 information about coding values of, or other data stored on, first sensor information element 218. Oximeter 102 may then obtain and compare the information from first sensor information element 218 and second sensor information element 134 to determine the security and reliability of sensor 106. If the elements do not correctly designate a single approved sensor, an audible and/or visual warning may be triggered. The addition of this second information element may serve to tie various portions of a single accessory, such as a sensor, together, thereby making it more difficult for a knock off manufacturer to scavenge parts, particularly if the parts are discarded separately. Alternatively, information from the cable information element 116 may indicate that an attached oximeter 102 should look for second sensor information element 134. Information contained in second information element 134 may then indicate whether or not a first sensor information element 218 is present and/or what data should be included thereon to indicate an authorized sensor.

In various embodiments, second sensor information element 134 may advantageously store some or all of a wide variety of information, including, for example, sensor type designation, patient information, sensor characteristics, software such as scripts or executable code, oximeter or algorithm upgrade information, or many other types of data. In a preferred embodiment, the second sensor information element 134 may also store useful life data indicating whether some or all sensor components have expired and should be replaced. In such an embodiment, the oximeter 102 may compare the information it received from first sensor information element 218 and second sensor information element 134 as before. Further it may also help aid in determining that sensor elements have not been used longer than their useful life based on the life data retrieved from second sensor information element 134. In such an embodiment, the oximeter 102 may also produce an audible or visual alarm if sensor life data from second sensor information element 134 indicates that some or all of sensor 106's components are out of date.

Similarly cable information element 116 may also include useful life data. This data can be used by oximeter 102 to help reduce the risk that cable 104 might be used longer than its safe life.

At least some embodiments including second information element 134 may include further protection against cannibalization of parts. Once a sensor including second information element 134 is attached and authorized, the LEDs should be immediately accessible for measurement by the patient monitor 102. In an embodiment, if at any time the second information element 134 is accessible but the LEDs are not, the patient monitor 102 may trigger an alert or an alarm and/or may disable the use of the component including the second information element 134. This may help to provide additional quality control protection because if the first and second information elements 218, 134 are cannibalized from old sensors, they are often placed in a generic cable or generic sensor adaptor. This generic adaptor often remains connected while generic sensors are replaced.

FIG. 4 illustrates one potential general layout of the first sensor information element 218, cable information element 116, and LEDs 222, 224. In such an embodiment, oximeter board 440 is the portion of the oximeter 102 that communicates with the cable 104 and sensor 106. In an embodiment, oximeter board 440 may preferably communicate with cable information element 116 via a serial transmission line 446. In FIG. 4, cable information element 116 is located in port connector 114 of the cable 104 in this embodiment. Once oximeter board 440 determines that it is connected to cable 104 providing information indicating that it should look for first sensor information element 218, it sends and receives signals down and from transmission lines 442, 444. Transmission lines 442, 444 pass the length of cable 104 into sensor 106 where first sensor information element 218 and LEDs 222, 224 are connected in parallel as described in more detail with respect to FIG. 2A.

FIG. 4 shows a possible distribution of the first sensor information element 218 and LEDs 222, 224 in the sensor. In the embodiment shown, first sensor information element 218 is located in the connection housing 112 where space is generally more readily available (as it is generally desirable to keep the sensor volume near the LED emitters 222, 224 and photodetector 226 as low as possible). Other placements for the elements, such as the first sensor information element 218 and LEDs 222, 224 on sensor 106, are also contemplated by this disclosure. Those of ordinary skill in the art would know that first sensor information element 218, for example, could be located anywhere in the sensor 106 or on separate transmission lines from those connecting the LEDs 222, 224 to the oximeter board 440.

FIG. 5 illustrates an embodiment of the layout for the cable 104 whose cable information element 116 indicates that a first sensor information element 218 and a second sensor information element 134 should be found in the sensor. In an embodiment, serial transmission line 446 connects the oximeter board 440 to the cable information element 116 as above. However, serial transmission line 446 also runs the length of cable 104 and connects to second sensor information element 134 located in sensor 106 in a multi-drop memory configuration. Oximeter board 440 may access cable information element 116 and second sensor information element 134 while running generally few transmission lines. If cable 104 is connected to a sensor 106 that does not have second sensor information element 134, the oximeter board 440 may advantageously determine that the sensor is unauthorized and also advantageously may not enable the sensor. The rest of the circuits (i.e. transmission lines 442, 444; first sensor information element 218; and LEDs 222, 224) are the same as in FIG. 4.

It is to be noted that FIGS. 4 and 5 are representative embodiments only. These figures are not meant to be read as the exact or only possible locations of the elements discussed. For example, first sensor information element 218 and/or second information element 134 may or may not be located in the same portion of the sensor. One or both or neither may be placed in or near the connection housing 112. It is also possible for them to be at other positions in the sensor. The roles of each may also be switched with either one or both containing information about data stored on the other. The numbering and discussion of the information elements is merely for ease of reference. It is also important to know that functionality of serial transmission line 446, as well as transmission lines 442, 444, may be accomplished through other means, such as, for example, public or private communications networks or computing systems, or various wired or wireless communications.

Requirement Tables

In an embodiment, an information element 116 includes data allowing the connection of both types of sensors depicted in FIG. 2 and FIG. 3. Thus, either a sensor 106 with only first information element 218 or one with both first information element 218 and second information element 134 could be connected as authorized sensors. In an embodiment, cable information element 116 may include a sensor requirement table as illustrated in Table 1 below. A sensor requirement table may list different types of attachable accessories (such as the sensors generally discussed) and designate which version of such sensors can be authorized. This may be accomplished through a single bit for each type. For example, as shown in Table 1, cable information element 116 may include a table with a list of bits designating whether or not an attached sensor must have a second information element 134—here a 1 indicates the second information element 134 is required, while a 0 indicates an attached accessory may have either the first information element 218 or both information elements. As shown in this example, disposable sensors must include the second information element 134, but reusable or combination sensors may include one or both sensor information elements. Any of a number of sensor or other accessories may be allowed or disallowed in such a manner. It is understood that the first sensor information element 218 must be capable of identifying the type of sensor that it is a part of for comparison to the requirement table, in such an embodiment.

TABLE 1

| Disposable | 1 |
| Reusable | 0 |
| Combination | 0 |
| Adult | 1 |
| Neonatal | 0 |
| ... | ... |
| Override | 0 |

Furthermore, in an embodiment, the requirement table may include an override bit or entry. The override bit preferably allows the attachment of both kinds of accessories for all types, regardless of the current values listed in the rest of the table. In such an embodiment, the override bit may allow diagnostics, testing, and the like without having to separately keep track of or lose the settings for the various accessory types. Those of skill in the art will understand from this disclosure that the requirement table functionality may be implemented in a number of ways. For example, the table may be stored in an accessory information element, such as cable information element 116, may be included in the monitor 102, and the like. Additionally the requirement table may be implemented as a table, linked list, array, single, multi-bit variable, or the like, and each entry may comprise one or more bits to store the information. In one embodiment, the requirement table may be stored on an EPROM, which may allow the table entries to be set only once. In another embodiment, an EEPROM or other rewritable memory may allow each table entry to be altered more than once.

Site Licenses

The transfer of accessories from location to location, the sale of used accessories, and the like can also make quality control more difficult, such as by making accessory use hard to track. As such, it is also possible to help maintain quality control by recording or maintaining site licenses, so that accessories, once used, can be tracked to their first use location or maintained at a specific location.

Many patient monitors have an associated device ID, typically this is a software ID, but IDs coded into hardware are also possible. In an embodiment of the present disclosure where the monitor has such an ID, accessory use may be tracked or controlled through use of the monitor ID. A general example will be set forth before turning to a specific embodiment according to the figures. When an accessory having an information element is plugged into the monitor having a monitor ID, the monitor may check to see if a monitor ID has been written to a portion of the information element. If not, the monitor may cause its own monitor ID to be written to the information element. From this point on, any monitor connected to that accessory will be able to determine the monitor of first use. If the accessory should later fail, an accessory or patient monitor manufacturer may then be able to determine where it was first used and if it was transferred to another location. In an embodiment, accessories may be tied to specific monitors or sets of monitors, such as to aid in keeping an accessory at a particular site or location. Once an accessory is used with a specific monitor, each monitor to which it is subsequently attached can read the monitor ID and determine if the monitor with which it was first used is part of the current monitor's grouping (e.g. a site license). Monitors can be programmed to recognize monitor IDs from a specific site (such as one hospital, a health system, etc.), a geographic area (such as by country), an Original Equipment Manufacturer (OEM), combinations of the same, and the like—anywhere from a single recognized monitor (itself) to any number of monitors. In an embodiment, the information element may include at least a portion with write once capability, such as an EPROM, so that the monitor ID that is first written to the information element cannot be changed.

Figure 7:
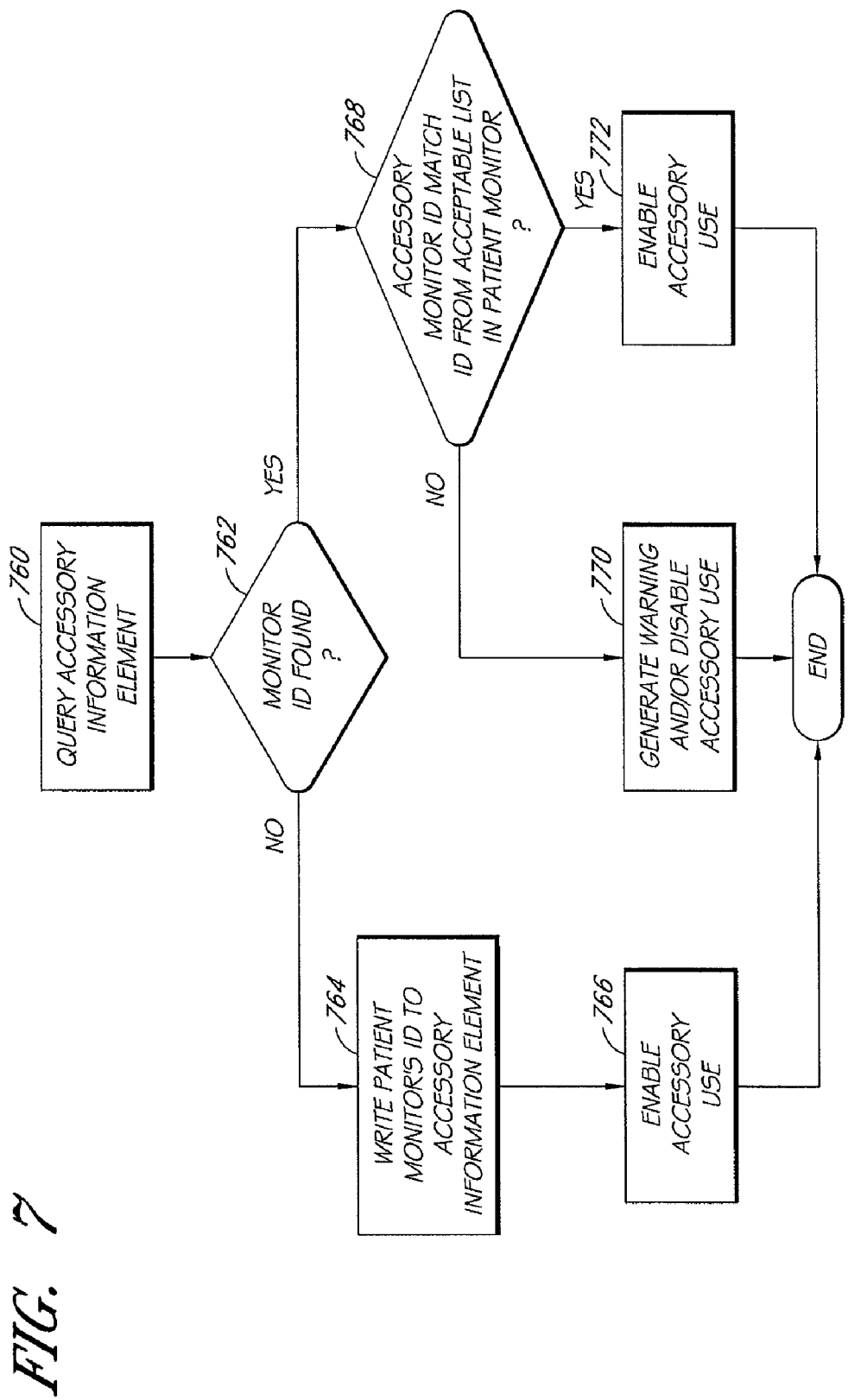
FIG. 7 illustrates a flow chart of an embodiment of a method utilizing quality control elements to enforce a site license.

A specific embodiment utilizing an oximeter example will now be discussed in reference to the Figures. In looking to FIGS. 5 and 7, oximeter board 440, has a monitor ID (not shown). When, for example, cable 104, having cable information element 116 is connected to oximeter board 440, the oximeter board may query cable information element 116 (block 760). If cable information element 116 has not been used before, in an embodiment, it will have free space to which data may be written (block 762, branching with no monitor ID found). Oximeter board 440 will then cause monitor ID to be written to the cable information element (block 764). (In an embodiment, a similar process may take place with sensor 106 and second sensor information element 134.) The monitor ID written to the cable information element 116 is preferably persistent, so as to remain when the cable 104 is disconnected from oximeter board 440. During each subsequent use of the cable 104, oximeter board 440 will be able to read the monitor ID from cable information element 116 (blocks 760, 762, branching with a monitor ID found). In an embodiment, the patient monitor then compares the monitor ID found with a list accessible by the oximeter board 440 (block 768). The oximeter board may respond according to the results of that ID comparison. For example, if the monitor ID found on the cable 104 is not acceptable, a warning may be generated or the oximeter board may not allow readings using the cable (block 770). Alternatively, if the cable contains an acceptable monitor ID, the oximeter may perform monitoring using the cable 104 (block 772).

For example, a hospital may have a site license that allows the cables it purchases to be used on any of its own oximeters. Each oximeter board 440 has its own monitor ID, but also has a list of monitor IDs of the other monitors the hospital owns or licenses. Once a cable is used with one of the hospital's oximeters, the cable 104 may only be able to work with that hospital's other oximeters. In one embodiment, connecting such a cable 104 to another hospital's oximeter will trigger a visual or audible warning. In another embodiment, use of the cable may be disabled. This type of quality control can help both the original hospital and the subsequent hospital in this example. If a cable fails, the first hospital can report it to the supplier who may be able to determine if the first hospital's oximeters may be the source of an underlying problem. On the other hand, the second hospital may be alerted to used accessories that may be more likely to fail.

There are numerous alternatives for such a "site license" quality control. For example, oximeters or other patient monitors may have specific lists of acceptable monitor IDs, monitor IDs may be the same for all patient monitors in a group, patient monitors may have a range of acceptable monitor IDs, patient monitors may have a specific equation or algorithm that determines acceptable monitor IDs, and the like. In some embodiments, accessories may record monitor IDs from all monitors to which they are connected, allowing manufacturers, suppliers, end users and the like to track the monitor's use.

Upgrade Tool

One specific accessory that may be utilized in a patient monitor system such as that described in the previous "Requirements Table" and "Site License" sections is an upgrade tool. Upgrade tools connect to an accessory port of a patient monitor to aid in reprogramming or updating the patient monitor without the need for an additional port, taking the patient monitor apart, returning it to the manufacturer and the like. Upgrade tools and a method for their use is generally disclosed in U.S. application Ser. No. 10/898,680, titled "Multipurpose Sensor Port" and filed on Jul. 23, 2004, incorporated herein by reference and made a part of this specification.

Often times a patient monitor or a specific control board will be made by an OEM that is capable of monitoring a host of patient parameters. Making all its boards the same can often reduce costs for an OEM. The OEM, however, may license only certain aspects of the patient monitor or control board to various users. For example, one hospital may obtain the equipment and license it to monitor $SpO_2$, while another may license only CO monitoring, and the like. Should a user wish to change its monitoring capabilities, the OEM does not need to sell it new equipment, instead it can just enable or disable various features of the patient monitor or control board that it has already provided to that user through use of an upgrade tool. It is important that such an upgrade tool only be enabled for specific patient monitors, however. For example, if hospital A pays for upgrades to its licenses, the OEM would like to ensure that the upgrade tool provided to A is not used to upgrade hospital B's patient monitors. The monitor ID recording discussed above is one way that this restriction can be accomplished. For example, an upgrade tool may record the monitor ID of the first monitor to which it is attached. In most instances, this will be a patient monitor from the proper upgrade group. Once this monitor ID is recorded, the upgrade tool may then only be enabled by any other patient monitor in the correct group, like any other accessory.

In other embodiments, an upgrade tool may contain an information element that stores the monitor IDs of all patient monitors for which an upgrade has been paid. The upgrade tool and patient monitor can then compare IDs to determine if the patient monitor qualifies for the upgrade. As another alternative, an upgrade tool may have a predetermined ID and all OEM patient monitors or boards that may utilize that upgrade tool may be loaded with an ID or software sufficient to match to the upgrade tool's ID during or sometime after manufacture. In other embodiments, a patient monitor may be upgraded by connection to a network, such as by telephone, cable, DSL, USB, FireWire, and the like. Additionally, in an embodiment, a patient monitor may allow a user to enter the monitor ID, such as via a keypad, keyboard, or touch screen interface.

An upgrade tool may be used to alter one or more requirements tables as well. However, it is also possible, in an embodiment, to program one or more accessories themselves to amend requirements tables or upgrade other programming. For example, a sensor information element 134 may include programming to alter a requirement table stored in a cable information element 116 once the components are connected and readied for monitoring.

Wireless Identification

Embodiments of the foregoing information elements use electrical connections to facilitate communication between the patient monitors and the information elements. This is also true in patient monitors that utilize disposable and reusable elements (such as pictured in FIG. 1). In sensors such as FIG. 1, it is often advantageous to control the quality of the disposable portions to reduce problems that may arise from inferior disposable portions, such as faulty attachment, improper alignment of sensor components, contamination of the measurement site through ambient light or physical contaminants, and the like. However, maintaining an electrical connection across the reusable/disposable mating point may complicate quality control efforts.

Wireless communications may offer additional advantages to help reduce reliance on electrical contacts and advantageously allow communication between disposable and other system elements. Wireless solutions include passive and active radio frequency identification (RF ID). Passive solutions get their broad ordinary meaning known to one skilled in the art, including solutions that rely on induction from surrounding electromagnetic waves, such as radio waves, to power the RF ID tag. Active solutions get their broad ordinary meaning known to one skilled in the art, including solutions that have an internal or external power source, such as a battery, photovoltaic cell, or electrical transmission lines to an exterior source of power.

A RF ID solution suitable for the purposes discussed here is generally commercially available. However, a brief discussion of the general technology is instructive. A basic RF ID tag includes an information element, such as an integrated circuit, coupled with an antenna. The antenna receives signals from a reader device capable of acquiring data from the integrated circuit of the tag. In passive RF ID, the incoming radio frequency energy from the reader device induces sufficient electrical current to power the information element and transmit a response indicative of the information stored on the information element. In active RF ID, a battery or other power source may be used to supplement or provide the power for transmitting the response.

Figure 6:
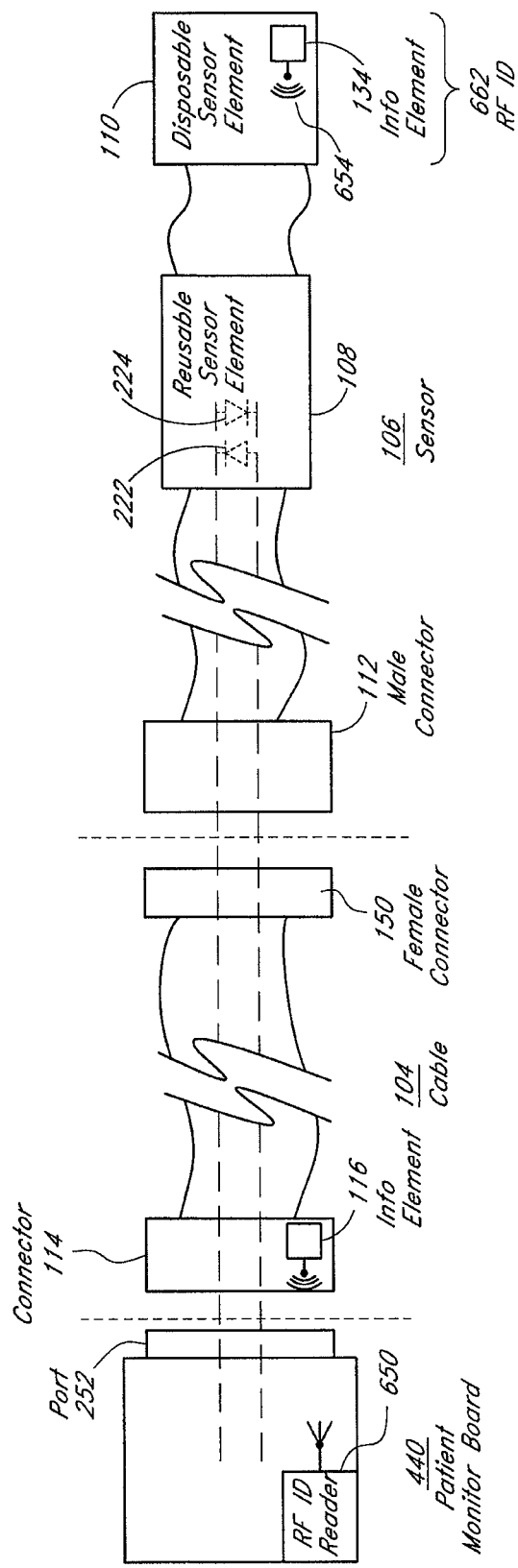
FIG. 6 illustrates an exemplary block diagram of an oximetry system including quality control devices utilizing wireless identification technology.

FIG. 6 illustrates an exemplary patient monitoring system incorporating wireless authentication utilizing radio frequency identification in relation to cable information element 116 and sensor information element 134. In one embodiment of this disclosure the RF ID configuration is passive, thereby simplifying a disposable portion of a sensor according to this disclosure. In another embodiment of this disclosure, the RF ID configuration may be active. While this creates a slightly more complicated cable, sensor or other accessory, there are advantages that may offset the complications. For example, active RF ID tags typically allow for greater memory and the ability to store data received from the reader. An active RF ID tag may also provide greater transmission distances.

Specifically looking to the differences in FIG. 6, oximeter board 440 further comprises or is in communication with a reader 650 capable of sending and receiving radio frequency signals to attached accessories. In the cable 104, information element 116 is now connected to a radio frequency antenna 652 to form a cable RF ID tag 660. Similarly, in the sensor 106, second information element 134 is also connected to a radio frequency antenna 654 to form a sensor RF ID tag 662. Because cable information element 116 and information element 134 may now communicate with each other and/or with oximeter board 440 (via reader 650) through radio frequency signals, there is no need to have serial transmission line 446 as was previously connecting these elements.

To enable attached accessories in an embodiment utilizing this technology, oximeter board 440 directs reader 650 to send out a radio frequency signal. In the cable 104, antenna 652 receives this signal, and redirects the energy to reply with a signal indicative of the information stored on cable information element 116. Incoming radio frequency signals induce a current in cable information element 116 and provide the power to transmit a response. Often this is done through back scattering the carrier signal from the reader 650. Oximeter board 440's reader 650 may also send out a radio frequency signal received by antenna 654 in sensor 106. Antenna 654 likewise redirects the energy received in accepting the signal to reply with a signal indicative of the information stored on information element 134. Reader 650 receives each of the signals generated by cable RF ID tag 660 and sensor RF ID tag 662 and communicates them to oximeter board 440. Oximeter board 440 compares the received information and enables usage of cable 104 and sensor 106 for patient monitoring if it recognizes each as approved accessories.

It is notable that the workings of the RF ID system as in FIG. 6 have been discussed in relation to passive RF ID elements. It would be straightforward for one of ordinary skill to modify either or both of cable RF ID tag 660 and sensor RF ID tag 662 to work as active RF ID tags by addition of a power source such as a battery or electrical transmission lines from the oximeter's power source. This may be necessary if the RF ID element needs to transmit more than an identification code or other small amount of data.

It should also be understood that the site license and upgrade tool concepts may also utilize wireless technology as described herein to read and write monitor IDs. In an embodiment, this may allow a patient monitor to update associated accessories without need of attaching the accessory to the patient monitor.

Although the patient monitor capable of maintaining quality control in an optical sensor is disclosed with reference to its preferred embodiments, the disclosure is not intended to be limited thereby. Rather, a skilled artisan will recognize from the disclosure herein a wide number of alternatives for such a patient monitor. For example, the elements used to code and identify the sensor may be passive or active such as resistors, transistor networks, memory chips, or other identification devices like Dallas Semiconductor DS 1990 or DS 2401 or other automatic identification chips. As described above, first and second sensor information elements may be switched in various embodiments, and one or the other may be included. Additionally, RF ID solutions are not the only wireless solutions available; other passive or active wireless communications may also be used such as those conforming to IEEE or Bluetooth® standards. It is also possible to alter the connections between various accessories; for example, the sensor's 106 male connection housing 112 and the cable's 104 female connection housing 150 may be reversed or may each have a male and female component. Furthermore, any of a number of accessories may include elements as described herein. Such accessories may be disposable or reusable or may have portions that are disposable and others that are reusable. Accessories may include, for example, cables, sensors, battery packs, data storage such as hard drives, flash drives, and the like, computer boards, and the like.

It is also noted that the disclosure herein discusses only a two LED, one photodetector configuration for straightforwardness of the disclosure. One skilled in the art would know that more complex or varied data may be retrieved through the addition of more LEDs or other emitting devices and/or more photodetectors or other detecting devices. Such devices may continue to utilize a single first sensor information element 218 or multiple information elements, corresponding to various sensor components, with or without a second sensor information element 134. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

Additionally, all publications, patents, and patent applications mentioned in this specification are herein incorporated by reference and made a part of the specification hereof to the same extent as if each individual publication, patent, or patent application was specifically and individually indicated to be incorporated by reference.

What is claimed is:

1. A patient monitoring system configured with improved quality control of its accessories through accessory authorization, the system comprising:
   a noninvasive sensor including a sensor information element storing sensor information;
   a cable, separate from and connectable with said noninvasive sensor including an information element storing cable information governing which information must at least be found in said sensor information;
   a patient monitor configured to receive a signal indicative of one or more physiological parameters of a patient from the sensor through the cable, the patient monitor further configured to acquire the cable information stored in the information element of the cable, to acquire sensor information from the noninvasive sensor, and to determine, based at least in part on the acquired cable and sensor information, whether the sensor and cable are compatible based on the acquired information.

2. The patient monitoring system of claim 1, wherein the sensor information element comprises a single wire memory.

3. The patient monitoring system of claim 1, wherein the noninvasive sensor includes a second sensor information element storing additional sensor information indicative of sensor authorization information and wherein the patient monitor is also configured to acquire the additional sensor information to determine whether the sensor information is valid.

4. The patient monitoring system of claim 3, wherein the cable information element stores a table indicating whether or not a specific type of noninvasive sensor must include the second sensor information element in order to be authorized.

5. The patient monitoring system of claim 1, wherein the cable information element and the sensor information element are configured to be connected in a multi-drop configuration.

6. The patient monitoring system of claim 1, wherein the noninvasive sensor further comprises at least one energy emitter and the at least one energy emitter and the sensor information element are electrically connected in parallel.

7. The patient monitoring system of claim 1, wherein the noninvasive sensor further comprises at least one emitter on a different communication line than the sensor information element.

8. The patient monitoring system of claim 1, wherein the noninvasive sensor further comprises a disposable portion and a reusable portion.

9. The patient monitoring of claim 8, wherein the sensor information element is located on the reusable portion.

10. The patient monitoring system of claim 8, wherein the sensor information element is located on the disposable portion.

11. A patient monitor system configured to ensure fidelity and compatibility in sensors accessories used by the monitor and to acquire sensor signals indicative of light attenuated by body tissue, the patient monitor system comprising: a first accessory including a first information element storing first information; a second accessory including a second information element storing second information; said first accessory and said second accessory are connectable to each other; and a patient monitor configured to communicate with said first accessory and said second accessory via said first accessory; wherein said patient monitor is configured to compare said first information with said second information and to determine, based at least in part on a result of the comparison, whether said first accessory and said second accessory are compatible with each other and with the patient monitor.

12. The patient monitor system of claim 11 wherein said first accessory comprises a cable.

13. The patient monitor system of claim 11 wherein said second accessory comprises a noninvasive sensor.

14. The patient monitor system of claim 11 further comprising a requirements table, wherein said requirements table indicates whether said second accessory must include a second authorization information element.

15. The patient monitor system of claim 14 wherein said requirements table is included in said first information element of said first accessory.

16. The patient monitor system of claim 14 wherein said at least one authorization information element comprises a resistor.

17. The patient monitor system of claim 16 wherein said second authorization information element comprises an EPROM.

18. The patient monitor system of claim 16 wherein said second authorization information element comprises an EEPROM.

19. The patient monitor system of claim 16 wherein said second authorization information element stores data which can be used to alter said requirements table.

* * * * *

UNITED STATES PATENT AND TRADEMARK OFFICE
CERTIFICATE OF CORRECTION

PATENT NO. : 8,255,026 B1
APPLICATION NO. : 11/871817
DATED : August 28, 2012
INVENTOR(S) : Ammar Al-Ali Page 1 of 1

It is certified that error appears in the above-identified patent and that said Letters Patent is hereby corrected as shown below:

In Column 1, Line 17, change "12," to --15,--.

In Column 1, Line 29, change "U.S. U.S." to --U.S.--.

In Column 1, Line 53, change "methenoglobin" to --methemoglobin--.

In Column 1, Line 54, change "billirubins," to --bilirubin,--.

In Column 1, Line 55, change "like" to --like.--.

In Column 16, Line 23, In Claim 9, after "monitoring" insert --system--.

In Column 16, Line 39, In Claim 11, change "information" to --information,--.

Signed and Sealed this
Nineteenth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,255,026 B1  
APPLICATION NO. : 11/871817  
DATED : August 28, 2012  
INVENTOR(S) : Ammar Al-Ali Page 1 of 1

It is certified that error appears in the above-identified patent and that said Letters Patent is hereby corrected as shown below:

In The Claims

In Column 16, Line 29, In Claim 11, after "in" delete "sensors".

Signed and Sealed this
Second Day of June, 2015

Michelle K. Lee
*Director of the United States Patent and Trademark Office*